United States Patent [19]

Tully

[11] Patent Number: 4,643,999
[45] Date of Patent: Feb. 17, 1987

[54] 2-SUBSTITUTED IMIDAZO[1,2-C]PYRIMIDINES HAVING ANXIOLYTIC PROPERTIES

[76] Inventor: Wilfred R. Tully, 5 Saint Peter's Rd., Cirencester, Gloucestershire, Great Britain

[21] Appl. No.: 681,948

[22] Filed: Dec. 14, 1984

[30] Foreign Application Priority Data

Dec. 22, 1983 [GB] United Kingdom ............... 8334210

[51] Int. Cl.$^4$ ................. A61K 31/505; C07D 471/02
[52] U.S. Cl. ...................................... 514/258; 544/281
[58] Field of Search ...................... 544/281, 236, 350; 514/258

[56] References Cited

U.S. PATENT DOCUMENTS

| | | | |
|---|---|---|---|
| 4,223,031 | 9/1980 | Covington et al. | 544/281 |
| 4,353,903 | 10/1982 | Fabiani et al. | 544/236 |
| 4,521,422 | 6/1985 | Dusza et al. | 514/258 |
| 4,532,243 | 7/1985 | Tully | 514/258 |

FOREIGN PATENT DOCUMENTS

| | | | |
|---|---|---|---|
| 0061380 | 9/1982 | European Pat. Off. | 544/281 |
| 0104104 | 3/1984 | European Pat. Off. | |

*Primary Examiner*—Donald G. Daus
*Assistant Examiner*—Stephen M. Kapner
*Attorney, Agent, or Firm*—Bierman and Muserlian

[57] ABSTRACT

Novel imidazo[1,2-c]pyrimidines of the formula

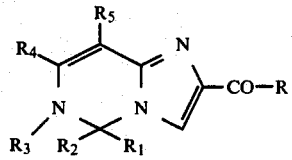

wherein R is an aryl of 6 to 12 carbon atoms, $R_1$ is selected from the group consisting of hydrogen and alkyl, alkoxy and alkylthio of 1 to 5 carbon atoms when $R_2$ and $R_3$ together form a carbon-nitrogen bond or $R_1$ and $R_2$ together are =O when $R_3$ is selected from the group consisting of hydrogen, alkyl of 1 to 5 carbon atoms and alkenyl of 2 to 5 carbon atoms, $R_4$ is selected from the group consisting of alkoxy and alkylthio of 1 to 5 carbon atoms, $R_5$ is selected from the group consisting of hydrogen and alkyl of 1 to 5 carbon atoms and their non-toxic, pharmaceutically acceptable acid addition salts having anxiolytic properties.

32 Claims, No Drawings

2-SUBSTITUTED IMIDAZO[1,2-C]PYRIMIDINES HAVING ANXIOLYTIC PROPERTIES

STATE OF THE ART

European Patent Application No. 0,061,380 describes imidazo[1,2-c]pyrimidines of the formula

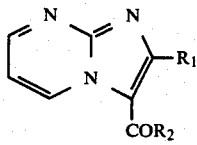

wherein $R_1$ and $R_2$ are alkyl, cycloalkyl or phenyl with 1 to 3 substituents or pyridyl or furyl or tetrahydrofuryl with at least one being a phenyl group having hypnotic activity.

Commonly assigned, copending U.S. patent application Ser. No. 526,046 filed Aug. 24, 1983 now U.S. Pat. No. 4,532,243 describes imidazo[1,2-a]pyrimidines of the formula

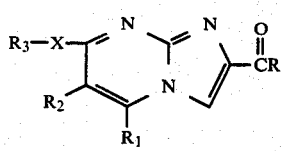

wherein X is oxygen or sulfur and R, $R_1$, $R_2$ and $R_3$ are various substituents having anxiolytic activity.

OBJECTS OF THE INVENTION

It is an object of the invention to provide the novel imidazo[1,2-c]pyrimidines of formula I and their non-toxic, pharmaceutically acceptable acid addition salts and a process for their preparation.

It is another object of the invention to provide novel anxiolytic compositions and a novel method of inducing anxiolytic activity in warm-blooded animals.

These and other objects and advantages of the invention will become obvious from the following detailed description.

THE INVENTION

The novel compounds of the invention are selected from the group consisting of imidazo[1,2-c]pyrimidines of the formula

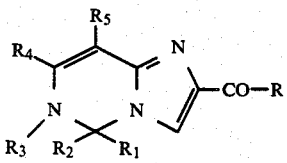

wherein R is an aryl of 6 to 12 carbon atoms, $R_1$ is selected from the group consisting of hydrogen and alkyl, alkoxy and alkylthio of 1 to 5 carbon atoms when $R_2$ and $R_3$ together form a carbon-nitrogen bond or $R_1$ and $R_2$ together are $=O$ when $R_3$ is selected from the group consisting of hydrogen, alkyl of 1 to 5 carbon atoms and alkenyl of 2 to 5 carbon atoms, $R_4$ is selected from the group consisting of alkoxy and alkylthio of 1 to 5 carbon atoms, $R_5$ is selected from the group consisting of hydrogen and alkyl of 1 to 5 carbon atoms and their non-toxic, pharmaceutically acceptable acid addition salts.

The alkyls of 1 to 5 carbon atoms include for example methyl, ethyl, propyl, isopropyl, butyl, isobutyl, tert.-butyl and pentyl while alkoxy of 1 to 5 carbon atoms includes methoxy, ethoxy, propoxy, isopropoxy, butoxy, isobutoxy, tert.-butoxy and pentoxy. Alkylthio of 1 to 5 carbon atoms includes methylthio, ethylthio, propylthio, isopropylthio, butylthio, isobutylthio, tert.-butylthio and pentylthio.

Aryl of 6 to 12 carbon atoms include phenyl and naphthyl, for example and alkenyl of 2 to 5 carbon atoms includes allyl for example.

Examples of suitable acids for the preparation of the acid addition salts are inorganic acids such as hydrochloric acid, hydrobromic acid, hydroiodic acid, nitric acid, sulfuric acid and phosphoric acid and organic acids such as formic acid, propionic acid, benzoic acid, maleic acid, fumaric acid, succinic acid, tartaric acid, citric acid, oxalic acid, glyoxylic acid, aspartic acid, alkane sulfonic acids such as methane sulfonic acid and aryl sulfonic acids such as benzenesulfonic acid.

Among the preferred compounds of formula I are those wherein R is phenyl, those wherein R is phenyl and $R_4$ is methoxy or methylthio, especially those wherein $R_2$ and $R_3$ form a nitrogen-carbon bond and those wherein R is phenyl, $R_4$ is methoxy or methylthio and $R_3$ is alkyl of 1 to 5 carbon atoms or alkenyl of 2 to 5 carbon atoms.

Specific preferred compound of formula I are 2-benzoyl-6-ethyl-7-methoxyimidazo[1,2-c]pyrimidin-5-one, 2-benzoyl-7-methoxy-6-propylimidazo[1,2-c]pyrimidin-5-one, (5-ethyl-7-methoxyimidazo[1,2-c]pyrimidin-2-yl)phenylmethanone, (7-methoxy-5-methylimidazo[1,2-c]pyrimidin-2-yl)phenylmethanone, 6-allyl-2-benzoyl-7-methoxyimidazo[1,2-c]pyrimidin-5-one, {7-methoxy-5-(methylthio)imidazo[1,2-c]pyrimidin-2-yl}-phenylmethanone, 2-benzoyl-6-ethyl-7-(methylthio)imidazo[1,2-c]pyrimidin-5-one and their non-toxic, pharmaceutically acceptable acid addition salts.

The novel process of the invention for the preparation of the compounds of formula I comprises cyclizing a compound of the formula

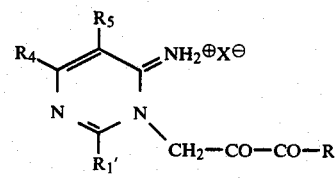

wherein $R_1'$ is hydrogen or alkyl, alkylthio or alkoxy of 1 to 5 carbon atoms, $X^\ominus$ is an anion such as halide and R, $R_4$ and $R_5$ are as defined above to obtain a compound of formula I wherein $R_3$ is hydrogen or together with $R_2$ is a carbon-nitrogen bond, followed, if desired, by reaction of a compound of formula I in which $R_3$ is hydrogen initially obtained with a compound of the formula $$A-R_3' \qquad \qquad IV$$

wherein A is halogen such as iodine and $R_3'$ is alkyl of 1 to 5 carbon atoms or alkenyl of 2 to 5 carbon atoms to obtain a compound of formula I in which $R_3$ is alkyl or alkenyl. The free base of formula I may optionally be converted to its acid addition salt by reaction with an approximately stoichiometric amount of an acid.

The anion $X^\ominus$ is preferably bromide and the reaction of the compounds of formulae I and IV is preferably effected in a solvent such as dimethylformamide with an alkyl iodide or alkenyl iodide in the presence of a base such as sodium hydride. The cyclization may be effected by refluxing in a solvent such as a lower alkanol.

In a preferred embodiment of the invention, a compound of formula V wherein $R_1'$ is alkoxy of 1 to 5 carbon atoms may be heated to more than 70° C. by refluxing in ethanol to obtain a compound of formula I wherein $R_1$ and $R_2$ are =O. To obtain a compound of formula I wherein $R_1$ is alkoxy of 1 to 5 carbon atoms, a compound of formula V wherein $R_1'$ is alkoxy of 1 to 5 carbon atoms is cyclized at a lower temperature such as at reflux in methanol. To obtain a compound of formula I wherein $R_1$ is hydrogen or alkyl or alkylthio of 1 to 5 carbon atoms, the corresponding compound of formula V is refluxed in ethanol.

The compounds of formula V may be prepared by reaction of a compound of the formula

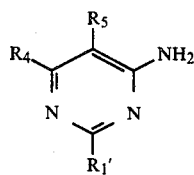

wherein $R_1'$, $R_4$ and $R_5$ are as defined above with a compound of the formula

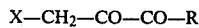
$$X-CH_2-CO-CO-R \quad \text{III}$$

wherein R is as defined above and X is an atom or group capable of elimination to form the anion $X^\ominus$ (e.g., a halogen, preferably bromine). The reaction is preferably carried out in the presence of an organic solvent such as tetrahydrofuran, ethyl ether or dimethoxyethane.

When they are not known per se, the compounds of formula II may, for example, be prepared by methods analagous to those described in Chem. Pharm. Bull., 1976, 24(3), 507; JACS, 1951, 73, 106; Chem. Ber., 1942, 75, 755; and Chem. Pharm. Bull., 1970, 18, 1385.

The reaction described above for the initial preparation of a compound of formula V can, if desired, be carried out so as to lead to the formation of a compound of formula I without intermediate isolation of the compound of formula V.

The above cyclization reactions of the compounds of formula V will lead in some cases to the formation of the compounds of formula I as free bases and in some cases to the formation of acid addition salts of the compounds of formula I (e.g. with the acid HX), depending on the basicity of the compounds formed. Where an acid addition salt is formed initially, the free base of formula I may be obtained from the acid addition salt, if desired without previous isolation, by treatment with a base such as an alkali metal hydroxide, bicarbonate or carbonate, e.g. potassium carbonate or sodium bicarbonate. A base of formula I may be converted into an acid addition salt by reacting the compound of formula I with an inorganic or organic acid, preferably in substantially stoichiometric proportions and the salts can be prepared if desired without intermediate isolation of the compound of formula I.

The compounds of formula III wherein X is halogen may, for example, be prepared by halogenating a compound of the formula

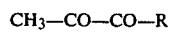
$$CH_3-CO-CO-R$$

wherein R is as defined above in the manner described in Helv. Chim. Acta, 1946, 29, 1247.

The compounds of the formula

$$CH_3-CO-CO-R$$

may, for example, be prepared by bromination of a compound of the formula

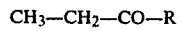
$$CH_3-CH_2-CO-R$$

followed by reaction with sodium methoxide to obtain a compound of the formula

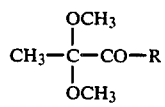

which is subsequently reacted with an acid such as hydrochloric acid to obtain the desired compound of formula $CH_3-CO-CO-R$.

The novel anxiolytically compounds of the invention are comprised of an anxiolytically effective amount of at least one compound of formula I and its non-toxic, pharmaceutically acceptable acid addition salts and a pharmaceutical carrier or excipient. The compositions may be in the form of tablets, dragees, capsules, gelatin capsules, granules, suppositories and injectable solutions or suspensions.

Examples of suitable excipients are talc, arabic gum, lactose, starch, magnesium stearate, cocoa butter, aqueous or non-aqueous vehicles, animal or vegetable fats, paraffin derivatives, glycols, various wetting agents, dispersants or emulsifiers and preservatives.

The compounds are useful for the treatment of anxiety states such as chronic anxiety accompanied by agitation, irritability or aggression, anxiety with insomnia and muscular tension and distress.

The novel method of the invention for relieving anxiety in warm-blooded animals, including humans, comprises administering to warm-blooded animals an anxiolytically effective amount of at least one compound of formula I and a non-toxic, pharmaceutically acceptable acid addition salt. The compounds may be administered orally, rectally or parenterally and the usual daily dose is 0.0015 to 3 mg/kg depending on the method of administration and the specific compound.

In the following examples there are described several preferred embodiments to illustrate the invention. However, it should be understood that the invention is not intended to be limited to the specific embodiments.

EXAMPLE 1

2-benzoyl-7-methoxy-imidazo[1,2-c]pyrimidin-5-one

STEP A: 1-phenyl-propane-1,2-dione 6.0 kg (44.78 moles) of propiophenone and 92 g of anhydrous aluminum chloride were added to 6 liters of ether followed by 17.2 kg (107.5 mole) of bromine at a rate to maintained a gentle reflux. When the addition was complete (approximately 6 hours), the mixture was heated to reflux overnight and then the solvent was removed under vacuum to obtain a lachrymatory dark red/orange oil. The oil was slowly added to a solution of 2.81 kg (122.2 mmole)of sodium in 45 l of methanol while maintaining the temperature below 20° C. When the addition was complete, 12.5 liters of concentrated hydrochloric acid were added and the mixture was stirred at room temperature for 1 hour. The precipitate was filtered off and the filtrate reduced in volume to approximately 25 liters by distillation of the methanol. The residue was partitioned between 10 liters of chloroform and 10 liters of water. Then, the organic phase was separated and the aqueous phase extracted twice with 5 liters of chloroform. The combined chloroform solutions were dried over sodium sulfate and evaporated to dryness. The residue was fractionally distilled under vacuum through a 30 cm Fenske column to obtain 5.7 kg of 1-phenylpropane-1,2-dione (86% yield) and a boiling point of 77°–85° C. at 1-2 mm Hg.

STEP B: 3-Bromo-1-phenylpropane-1,2-dione 5.32 kg of 1-phenylpropane-1,2-dione (98.6% by G.C. equivalent to 5.24 kg, 35.4 mole) were dissolved in 36 liters of chloroform and the solution was heated to 50° C. A solution of 5.66 kg (35.4 mole) of bromine in 8 liters of chloroform was added slowly to maintain a gentle reflux and immediate decolorization of the bromine (approximately 6 hours). The solution was cooled to room temperature overnight and was washed with 20 liters of saturated sodium bicarbonate solution and 20 liters of water and dried over sodium sulfate. The solvent was removed under vacuum to obtain 8.2 kg (100% yield) of a green/yellow oil which was used directly for subsequent reactions after estimation of its purity (approximately 75% by G.C. or N.M.R.).

STEP C:
2-Benzoyl-7-methoxy-imidazo[1,2-c]pyrimidin-5-one

A stirred solution of 10 g of 2,6-dimethoxy-4-pyrimidinamine in 25 ml of dry tetrahydrofuran was treated with a solution of 21 g of 3-bromo-1-phenyl-1,2-propanedione in 50 ml of dry diethyl ether. After stirring overnight, 20 ml of diethyl ether were added and the mixture was chilled and filtered to obtain 16.7 g of the crystalline pyrimidinium salt. A solution of 10 g of the salt in 30 ml of ethanol was refluxed for 2 hours under nitrogen, cooled, and diluted with 30 ml of diethyl ether. The mixture was chilled and filtered to obtain 4.4 g of 2-benzoyl-7-methoxy-imidazo[1,2-c]pyrimidin-5-one as a yellow crystalline solid melting at 208°–10° C. A further 1.4 g were obtained by chromatographing the residue after evaporation of the filtrate in ethyl acetate on silica.

EXAMPLE 2

2-benzoyl-6-ethyl-7-methoxyimidazo[1,2-c]pyrimidin-5-one

A stirred solution of 11 g of 2-benzoyl-7-methoxyimidazo[1,2-c]pyrimidin-5-one in 33 ml of dry dimethylformamide was treated with 1.27 g of 80% of sodium hydride and was stirred for another hour. 8 g of iodoethane were added dropwise over 10 minutes and stirring was continued for two hours after which the mixture was poured into iced water. The mixture was filtered to obtain 2.3 g of 6-ethyl-7-methoxyimidazo[1,2-c]pyrimidin-5-one as a yellow crystalline solid melting at 159°–60° C.

EXAMPLE 3

2-benzoyl-7-methoxy-6-propyl-imidazo[1,2-c]pyrimidin-5-one

Using the procedure of Example 2, 2-benzoyl-7-methoxyimidazo[1,2-c]pyrimidin-5-one and iodopropane were reacted to obtain 2-benzoyl-7-methoxy-6-propyl-imidazo[1,2-c]pyrimidin-5-one. Spectral, yield and melting point data are given in Table I.

EXAMPLE 4

(7-methoxy-5-methyl-imidazo[1,2-c]pyrimidin-2-yl)-phenylmethanone

A stirred solution of 2.1 g of 6-methoxy-2-methyl-4-pyrimidinamine in dry tetrahydrofuran was treated with a solution of 5.4 g of 3-bromo-1-phenyl-1,2-propanedione in 5 ml of dry ether. After stirring overnight, the mixture was chilled and the precipitated salt filtered off. A suspension of the salt in dry ethanol was refluxed for 1.5 hours, chilled, and filtered. The solid was shaken with a mixture of chloroform and aqueous sodium bicarbonate and the organic layer was evaporated to dryness under reduced pressure. The residue was chromatographed in ethyl acetate on silica to obtain 2.7 g of (7-methoxy-5-methyl-imidazo[1,2-c]pyrimidin-2-yl)-phenylmethanone as a yellow crystalline solid melting at 165°–7° C.

EXAMPLES 5 TO 15

Using methods similar to those used in Examples 1, 2 or 4 (designated methods A,B and C respectively in Table I below) but starting from the corresponding compounds of formula II, or from the corresponding compounds of formula I, wherein $R_3$ is hydrogen the compounds of Examples 5 to 9 and 12 to 15 were prepared. The compound of Example 10 was prepared by a method (denoted A* in Table I below) analogous to that of Example 1 but using methanol rather than ethanol in the cyclization step. The compound of Example 11 was obtained as a by-product of Example 2 but could more efficiently be prepared by method A*. Spectral, yield, melting point and analytical data are also given in Table I.

EXAMPLE 5: (5-ethyl-7-methoxy-imidazo[1,2-c]pyrimidin-2-yl)phenylmethanone.

EXAMPLE 6: 2-benzoyl-7-ethoxy-imidazo[1,2-c]pyrimidin-5-one.

EXAMPLE 7: 2-benzoyl-7-methoxy-6-methyl-imidazo[1,2-c]pyrimidin-5-one.

EXAMPLE 8: (7-methoxy-5,8-dimethyl-imidazo[1,2-c]pyrimidin-2-yl)phenylmethanone.

EXAMPLE 9: 6-allyl-2-benzoyl-7-methoxy-imidazo[1,2-c]pyrimidin-5-one.

EXAMPLE 10: (5,7-dimethoxy-imidazo[1,2-c]pyrimidin-2-yl) phenylmethanone.

EXAMPLE 11: (5-ethoxy-7-methoxy-imidazo[1,2-c]pyrimidin-2-yl) phenylmethanone.

EXAMPLE 12: {7-methoxy-5-methylthio-imidazo[1,2-c]pyrimidin-2-yl}phenylmethanone.

EXAMPLE 13: {5,7-bis(methylthio)-imidazo[1,2-c]pyrimidin-2-yl}phenylmethanone.

EXAMPLE 14: 2-benzoyl-6-ethyl-7-methylthio-imidazo[1,2-c]pyrimidin-5-one.

EXAMPLE 15: 6-allyl-2-benzoyl-7-methylthio-imidazo[1,2-c]pyrimidin-5-one.

TABLE I

| Ex. | R | $R_1$ | $R_2$ | $R_3$ | $R_4$ | $R_5$ | Method | Yield % | IR cm$^{-1}$ (KBr disc) |
|---|---|---|---|---|---|---|---|---|---|
| 1 | Ph | | =O | H | $CH_3O$ | H | A | 64 | 1640,1670,1650,1610 |
| 2 | Ph | | =O | $C_2H_5$ | $CH_3O$ | H | B | 19 | 1700,1640,1600,1580 |
| 3 | Ph | | =O | $C_3H_7$ | $CH_3O$ | H | B | 18 | 1710,1630,1600,1580 |
| 4 | Ph | $CH_3$ | = | | $CH_3O$ | H | C | 67 | 1645,1635,1595,1575 |
| 5 | Ph | $C_2H_5$ | = | | $CH_3O$ | H | C | 45 | 1640,1600,1560,1500 |
| 6 | Ph | | =O | H | $C_2H_5O$ | H | A | 20 | 1730,1670,1650,1600 |
| 7 | Ph | | =O | $CH_3$ | $CH_3O$ | H | B | 40 | 1710,1625,1600,1570 |
| 8 | Ph | $CH_3$ | = | | $CH_3O$ | $CH_3$ | C | 44 | 1640,1630,1600,1580 |
| 9 | Ph | | =O | $CH_2=CHCH_2$ | $CH_3O$ | H | B | 26 | 1710,1660,1630,1590 |
| 10 | Ph | $CH_3O$ | = | | $CH_3O$ | H | A* | 71 | 1650,1630,1600,1570 |
| 11 | Ph | $C_2H_5O$ | = | | $CH_3O$ | H | B | 0.3 | 1660,1640,1600,1590 |
| 12 | Ph | $CH_3S$ | = | | $CH_3O$ | H | C | 29 | 1640,1620,1515,1460 |
| 13 | Ph | $CH_3S$ | = | | $CH_3S$ | H | C | 25 | 1640,1600,1580,1520 |
| 14 | Ph | | =O | $C_2H_5$ | $CH_3S$ | H | B | 47 | 1680,1635,1600,1580 |
| 15 | Ph | | =O | $CH_2=CH-CH_2-$ | $CH_3S$ | H | B | 52 | 1690,1635,1595 |

| Ex. | M.p. | Formula | M. Wt. | C (Theory/Found) | H | N | S |
|---|---|---|---|---|---|---|---|
| 1 | 208–10° C. | $C_{14}H_{11}N_3O_3$ | 269.3 | 62.45/62.19 | 4.12/4.15 | 15.16/15.38 | |
| 2 | 159–60° C. | $C_{16}H_{15}N_3O_3$ | 297.3 | 64.64/64.66 | 5.09/5.09 | 14.13/14.15 | |
| 3 | 106–7° C. | $C_{17}H_{17}N_3O_3$ | 311.3 | 65.58/65.59 | 5.51/5.77 | 13.50/13.38 | |
| 4 | 165–7° C. | $C_{15}H_{13}N_3O_2$ | 267.3 | 67.41/67.2 | 4.90/4.98 | 15.72/15.65 | |
| 5 | 152–3° C. | $C_{16}H_{15}N_3O_2$ | 281.3 | 68.31/68.19 | 5.37/5.44 | 14.94/14.91 | |
| 6 | 218–20° C. | $C_{15}H_{13}N_3O_3$ | 283.3 | 63.60/63.58 | 4.62/4.58 | 14.83/14.56 | |
| 7 | 187–9° C. | $C_{15}H_{13}N_3O_3$ | 283.3 | 63.60/63.47 | 4.62/4.70 | 14.68/14.87 | |
| 8 | 185–7° C. | $C_{16}H_{15}N_3O_2$ | 281.3 | 68.31/68.38 | 5.37/5.16 | 14.94/14.96 | |
| 9 | 139–41° C. | $C_{17}H_{15}N_3O_3$ | 309.3 | 66.01/65.82 | 4.89/4.97 | 13.58/13.56 | |
| 10 | 141–3° C. | $C_{15}H_{13}N_3O_3$ | 283.3 | 63.60/63.73 | 4.62/4.63 | 14.83/14.90 | |
| 11 | 116–8° C. | $C_{16}H_{15}N_3O_3$ | 297.3 | 64.64/64.55 | 5.09/5.08 | 14.13/14.19 | |
| 12 | 149–50° C. | $C_{15}H_{13}N_3O_2S$ | 299.35 | 60.19/60.18 | 4.38/4.43 | 14.04/14.06 | 10.71/10.63 |
| 13 | 154–5° C. | $C_{15}H_{13}N_3OS_2$ | 315.4 | 57.12/57.28 | 4.15/4.20 | 13.32/13.32 | 20.33/20.06 |
| 14 | 152–4° C. | $C_{16}H_{15}N_3O_2S$ | 313.4 | 61.32/61.70 | 4.82/4.86 | 13.41/13.38 | 10.23/10.29 |
| 15 | 161° C. | $C_{17}H_{15}N_3O_2S$ | 325.4 | 62.75/62.77 | 4.65/4.73 | 12.93/12.86 | 9.85/9.77 |

EXAMPLE 16

Tablets were prepared containing 20 mg of the product of Example 2 or Example 5 and sufficient excipient of lactose, starch, talc and magnesium stearate for a final tablet weight of 150 mg.

PHARMACOLOGICAL DATA (1) Biochemical Activity

The affinity of the compounds for the benzodiazepine receptor was assessed using the radioligand [$^3$H] flunitrazepam and modifications of the original radio receptor binding method of Squires and Braestrup [Nature, Vol. 266 (1977) p. 732]. The values given in Table II are nanomolar concentrations of test drug which inhibited the specific binding of 0.6 nM [$^3$H] flunitrazepam to rat forebrain membrane preparations by 50% (IC$_{50}$nM).

(2) Anxiolytic Activity

Screening for anxiolytic activity was carried out by modifications of the conflict method of Geller et al [Psychopharmacologia, (1960), Vol. I, p. 482]. The values given in Table II are the minimum effective doses at which there was an observed increase in shocks above control (MED mg/kg po).

TABLE II

| EXAMPLE | RECEPTOR BINDING (IC$_{50}$nM) | GELLER CONFLICT (MED mg/kg po) |
|---|---|---|
| 2 | 2000 | 2 |
| 3 | 1000 | 10 |
| 4 | 520 | 50 |
| 5 | 215 | 10 |
| 9 | 500 | 5 |
| 10 | 1000 | 10 |
| 11 | 890 | — |
| 12 | 126 | 5 |
| 13 | 18 | 50 |
| 14 | 140 | 5 |
| 15 | 120 | 50 |

Various modifications of the compounds and methods of the invention may be made without departing from the spirit or scope thereof and it is to be understood that the invention is intended to be limited only as defined in the appended claims.

What I claim is:

1. A compound selected from the group consisting of imidazo[1,2-c]pyrimidines of the formula

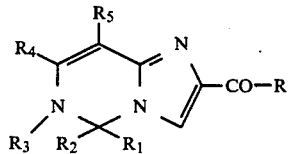

wherein R is phenyl or naphthyl, $R_1$ is selected from the group consisting of hydrogen and alkyl, alkoxy and alkylthio of 1 to 5 carbon atoms when $R_2$ and $R_3$ together form a carbon nitrogen bond or $R_1$ and $R_2$ together are =O when $R_3$ is selected from the group consisting of hydrogen, alkyl of 1 to 5 carbon atoms and alkenyl of 2 to 5 carbon atoms, $R_4$ is selected from the group consisting of alkoxy and alkylthio of 1 to 5 carbon atoms, $R_5$ is selected from the group consisting of hydrogen and alkyl of 1 to 5 carbon atoms and their non-toxic, pharmaceutically acceptable acid addition salts.

2. A compound of claim 1 wherein R is phenyl.

3. A compound of claim 2 wherein $R_4$ is $CH_3O-$ or $CH_3S-$.

4. A compound of claim 3 wherein $R_2$ and $R_3$ form a carbon-nitrogen bond.

5. A compound of claim 3 wherein $R_3$ is alkyl of 1 to 5 carbon atoms.

6. A compound of claim 3 wherein $R_3$ is alkenyl of 2 to 5 carbon atoms.

7. A compound of claim 1 selected from the group consisting of 2-benzoyl-6-ethyl-7-methoxy-imidazo[1,2-c]pyrimidin-5-one and its non-toxic, pharmaceutically acceptable acid addition salts.

8. A compound of claim 1 selected from the group consisting of 2-benzoyl-7-methoxy-6-propyl-imidazo[1,2-c]pyrimidin-5-one and its non-toxic, pharmaceutically acceptable acid addition salts.

9. A compound of claim 1 selected from the group consisting of (5-ethyl-7-methoxy-imidazo[1,2-c]pyrimidin-2-yl) phenylmethanone and its non-toxic, pharmaceutically acceptable acid addition salts.

10. A compound of claim 1 selected from the group consisting of (7-methoxy-5-methyl-imidazo[1,2-c]pyrimidin-2-yl) phenylmethanone and its non-toxic, pharmaceutically acceptable acid addition salts.

11. A compound of claim 1 selected from the group consisting of 6-allyl-2-benzoyl-7-methoxy-imidazo[1,2-c]pyrimidin-5-one and its non-toxic, pharmaceutically acceptable acid addition salts.

12. A compound of claim 1 selected from the group consisting of (7-methoxy-5-methylthio-imidazo[1,2-c]pyrimidin-2-yl)phenylmethanone and its non-toxic, pharmaceutically acceptable acid addition salts.

13. A compound of claim 1 selected from the group consisting of 2-benzoyl-6-ethyl-7-methylthio-imidazo[1,2-c]pyrimidin-5-one and its non-toxic, pharmaceutically acceptable acid addition salts.

14. An anxiolytic composition comprising an anxiolytically effective amount of at least one compound of claim 1 and a pharmaceutical carrier.

15. A composition of claim 14 wherein R is phenyl.

16. A composition of claim 15 wherein $R_4$ is $CH_3O-$ or $CH_3S-$.

17. A composition of claim 16 wherein $R_2$ and $R_3$ form a carbon-nitrogen bond.

18. A composition of claim 16 wherein $R_3$ is alkyl of 1 to 5 carbon atoms.

19. A composition of claim 16 wherein $R_3$ is alkenyl of 2 to 5 carbon atoms.

20. A method of inducing anxiolytic activity in warm-blooded animals comprising administering to warm-blooded animals an anxiolytically effective amount of at least one compound of claim 1.

21. A method of claim 20 wherein R is phenyl.

22. A method of claim 21 wherein $R_4$ is $CH_3O-$ or $CH_3S-$.

23. A method of claim 22 wherein $R_2$ and $R_3$ form a carbon-nitrogen bond.

24. A method of claim 22 wherein $R_3$ is alkyl of 1 to 5 carbon atoms.

25. A method of claim 22 wherein $R_3$ is alkenyl of 2 to 5 carbon atoms.

26. A method of claim 20 wherein the compound is selected from the group consisting of 2-benzoyl-6-ethyl-7-methoxy-imidazo[1,2-c]pyrimidin-5-one and its non-toxic, pharmaceutically acceptable acid addition salts.

27. A method of claim 20 wherein the compound is selected from the group consisting of 2-benzoyl-7-methoxy-6-propyl-imidazo[1,2-c]pyrimidin-5-one and its non-toxic, pharmaceutically acceptable acid addition salts.

28. A method of claim 20 wherein the compound is selected from the group consisting of (5-ethyl-7-methoxy-imidazo[1,2-c]pyrimidin-2-yl)phenylmethanone and its non-toxic, pharmaceutically acceptable acid addition salts.

29. A method of claim 20 wherein the compound is selected from the group consisting of (7-methoxy-5-methyl-imidazo[1,2-c]pyrimidin-2-yl)phenylmethanone and its non-toxic, pharmaceutically acceptable acid addition salts.

30. A method of claim 20 wherein the compound is selected from the group consisting of 6-allyl-2-benzoyl-7-methoxy-imidazo[1,2-c]pyrimidin-5-one and its non-toxic, pharmaceutically acceptable acid addition salts.

31. A method of claim 20 wherein the compound is selected from the group consisting of {7-methoxy-5-methylthio-imidazo[1,2-c]pyrimidin-2-yl}phenylmethanone and its non-toxic, pharmaceutically acceptable acid addition salts.

32. A method of claim 20 wherein the compound is selected from the group consisting of 2-benzoyl-6-ethyl-7-methylthio-imidazo[1,2-c]pyrimidin-5-one and its non-toxic pharmaceutically acceptable acid addition salts.

* * * * *